United States Patent [19]

Kinsho et al.

[11] Patent Number: 5,693,841
[45] Date of Patent: *Dec. 2, 1997

[54] CYCLOHEXANONE COMPOUNDS, PROCESS FOR PREPARING THE SAME, AND PROCESSES FOR PREPARING SILACYCLOHEXANE-BASED LIQUID CRYSTAL COMPOUNDS FROM THE CYCLOHEXANONE COMPOUNDS

[75] Inventors: Takeshi Kinsho; Takaaki Shimizu; Tsutomu Ogihara; Mutsuo Nakashima; Tatsushi Kaneko, all of Niigata-ken, Japan

[73] Assignee: Shin-Etsu Chemical Co., Ltd., Tokyo, Japan

[*] Notice: The term of this patent shall not extend beyond the expiration date of Pat. No. 5,514,824.

[21] Appl. No.: 483,034

[22] Filed: Jun. 7, 1995

[30] Foreign Application Priority Data

Jun. 13, 1994 [JP] Japan ................... 6-154219

[51] Int. Cl.$^6$ ................................................. C07F 7/02
[52] U.S. Cl. ................................................. 556/406
[58] Field of Search ................................................. 556/406

[56] References Cited

U.S. PATENT DOCUMENTS 5,514,824   5/1996   Kinsho et al. .................... 556/406

FOREIGN PATENT DOCUMENTS 0630903   12/1994   European Pat. Off. .

OTHER PUBLICATIONS

Journal of Organometallic Chemistry, vol. 133, 1977, pp. 7-17, Washburne, S.S. et al., Acetolysis of 4,4-Disubstituted 4-silacyclohexyl Tosylates: Effect of Remote Silicon Substitution on Organic Reactivity.

Gilbert Stork et al, The Enamine Alkylation and Acylation of Carbonyl Compounds, J. Amer. Chem. Soc., 85, 1963, pp.207-222.

*Primary Examiner*—Jeffrey C. Mullis
*Attorney, Agent, or Firm*—Lowe, Price, LeBlanc & Becker

[57] ABSTRACT

A cyclohexanone compound of the following general formula (I) is provided

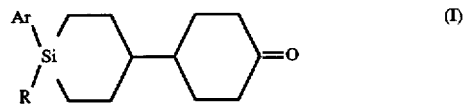

wherein Ar represents a phenyl group or a tolyl group, and R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms. The preparation of the cyclohexanone compound is also described along with processes for preparing liquid crystal compounds from the cyclohexanone compound.

17 Claims, No Drawings

CYCLOHEXANONE COMPOUNDS, PROCESS FOR PREPARING THE SAME, AND PROCESSES FOR PREPARING SILACYCLOHEXANE-BASED LIQUID CRYSTAL COMPOUNDS FROM THE CYCLOHEXANONE COMPOUNDS

BACKGROUND OF THE INVENTION

1. Field of the Invention

This invention relates to a novel cyclohexanone compound and preparation thereof and also to processes for preparing silacyclohexane-based liquid crystal compounds from the cyclohexanone compounds.

2. Description of the Prior Art

The liquid crystal display devices make use of optical anisotropy and dielectric anisotropy of liquid crystal substances. Depending on the mode of display, there are a variety of display systems including those of a twisted nematic type (TN type), a supertwisted nematic type (STN type), a super birefringence type (SBE type), a dynamic scattering type (DS type), a guest/host type, a type of deformation of aligned phase (DAP type), a polymer dispersion type (PD type), and an optical mode interference type (OMI type). The most popular display device is one which is based on the Schadt-Helfrich effect and has a twisted nematic structure.

Although the properties of the liquid crystal substances used in these liquid crystal devices depend, more or less, on the type of display, it is commonly required that the liquid crystal substances have a wide range of liquid crystal working temperatures and that they be stable against moisture, air, light, heat, electric field and the like. Moreover, the liquid crystal substances should desirably be low in viscosity and should ensure a short address time, a low threshold voltage and a high contrast in a cell. As the liquid crystal display devices have wider utility in recent years, the characteristic properties required for liquid crystal materials become much severer. In addition, those characteristics which have never been required for conventional liquid crystal substances are now expected such as a lower drive voltage, a wider working temperature range which could satisfy the on-vehicle needs and an improvement in low temperature performance.

Under these circumstances, we developed novel liquid crystal compounds which contain a silicon atom in the molecule so that the characteristic properties for use as a liquid crystal substance are improved, and proposed the liquid crystal compounds in our earlier Japanese Patent Application as will be set out hereinafter.

SUMMARY OF THE INVENTION

It is an object of the invention to provide a cyclohexanone compound which is an intermediate compound useful for preparing silacyclohexane-based liquid crystal compounds.

It is another object of the invention to provide a process for preparing a cyclohexanone compound of the type mentioned above.

It is a further object of the invention to provide a process for preparing a silacyclohexane-based liquid crystal compound, which is a kind of derivative of the cyclohexanone compound, from the cyclohexanone intermediate compound.

The above objects can be achieved, according to one embodiment of the invention, by a cyclohexanone compound of the following formula (I)

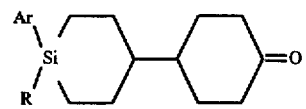

wherein Ar represents a phenyl group or a tolyl group, and R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms.

The cyclohexanone compound of the formula (I) is prepared according to a process which comprises:

subjecting an enamine compound of the following general formula (1)

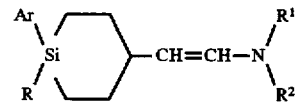

wherein $R^1$ and $R^2$, each, represent an alkyl group having from 1 to 4 carbon atoms or $R^1$ and $R^2$ may join to represent a group of —$(CH_2)_4$—, —$(CH_2)_5$— or —$(CH_2)_2O(CH_2)_2$— thereby completing a cyclic ring along with the nitrogen atom bonded therewith, and methyl vinyl ketone to Michael addition reaction to obtain Michael's adduct of the following general formula (2)

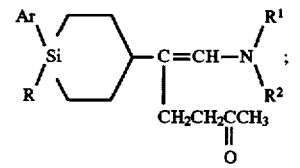

further subjecting the Michael adduct to intramolecular aldol condensation reaction or hydrolysis to obtain an aldehyde compound of the following general formula (3)

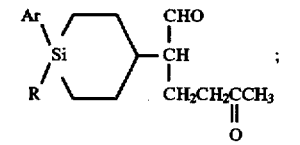

and subjecting the aldehyde compound to intramolecular aldol condensation reaction to obtain a cyclohexenone compound of the following general formula

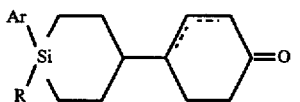

hydrogenating the cyclohexenone compound to obtain a cyclohexanone of the afore-indicated general formula (I).

According to another embodiment of the invention, there is provided a process for preparing a silacyclohexane-based liquid compound of the following general formula (II) from the cyclohexanone compound of the formula (I)

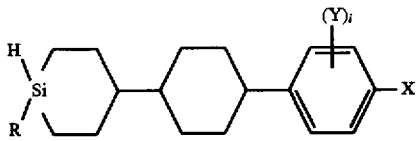
(II)

wherein R has the same meaning as defined with respect to the formula (I) and represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms, X represents CN, F, Cl, Br, $CF_3$, $OCF_3$, $OCHF_2$, $OCHFCl$, $OCF_2Cl$, $CF_2Cl$, $(O)_mCY_1=CX_1X_2$ wherein m is a value of 0 or 1, $Y_1$ and $X_1$, each, represent, H, F or Cl, and $X_2$ represents F or Cl, $O(CH_2)_r(CF_2)_sX_3$ wherein r and s are, respectively, a value of 0, 1 or 2 provided that r+s=2, 3 or 4, and $X_3$ represents H, F or Cl, or R or OR wherein R has the same meaning as defined above, Y represents a halogen, preferably F or Cl, or $CH_3$, and i is a value of 0, 1 or 2, the process comprising the steps of:

reacting the cyclohexanone of the general formula (I) with an organometal reagent of the following formula (5)

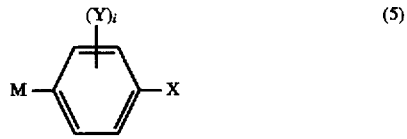
(5)

wherein M represents Li MgU, ZnU or $TiU_k(OW)_{3-k}$ wherein U represents a halogen, preferably Cl, Br or I, W represents an alkyl group preferably having from 1 to 6 carbon atoms, and k is zero or an integer of 1 to 3, and X, Y and i independently have the same meanings as defined with respect to the formula (II), thereby obtaining a compound of the following general formula (6)

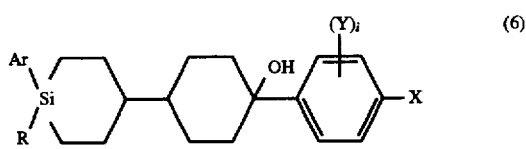
(6)

wherein At, R, Y, X and i independently have the same meanings as defined above;

subjecting the compound of the formula (6) to hydrogenolysis or hydrogenation after dehydration to obtain a compound of the following general formula (7)

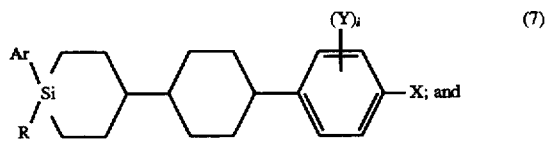
(7)

further subjecting the compound of the formula (7) to de-silylation and reduction to obtain a silacyclohexane-based liquid crystal compound of the afore-indicated general formula (II).

According to a further embodiment of the invention, there is also provided a process for preparing another type of silacyclohexane-based liquid crystal compound of the following general formula (III)

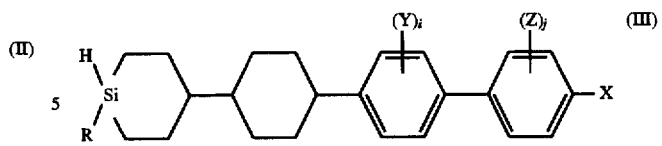
(III)

wherein R, Y, X and i independently have the same meanings as defined with respect to the formula (II), Z represents a halogen, preferably F or Cl, or $CH_3$, and i represents a value of 0, 1 or 2, the process comprising the steps of:

reacting the cyclohexanone compound of the aforeindicated formula (I) with an organometal reagent of the following general formula (8)

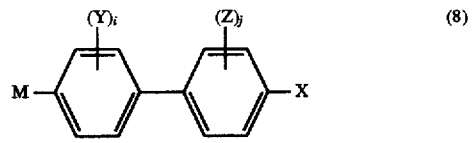
(8)

wherein M represents Li MgU, ZnU or $TiU_k(OW)_{3-k}$ wherein U represents a halogen, preferably Cl, Br or I, W represents an alkyl group preferably having from 1 to 6 carbon atoms, and k is zero or an integer of 1 to 3, X, i and j have, respectively, the same meanings as defined hereinbefore, thereby obtaining a compound of the following general formula (9)

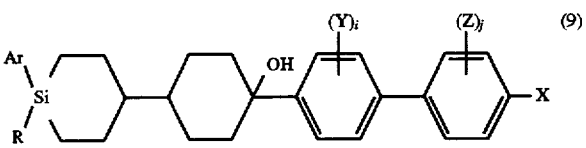
(9)

wherein Ar, R, X, Y, Z, i and i have, respectively, the same meanings as defined hereinbefore, subjecting the compound of the formula (9) to hydrogenolysis or hydrogenation after dehydration to obtain a compound of the following general formula (10)

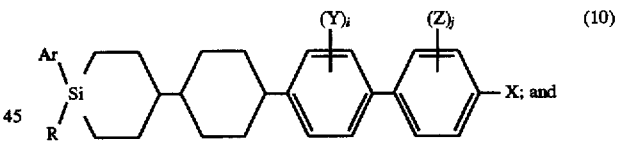
(10)

further subjecting the compound of the formula (10) to de-silylation and then to reduction to obtain a silacyclohexane-based liquid crystal compound of the afore-indicated formula (III).

According to a still further embodiment of the invention, the silacyclohexane-based liquid crystal compound of the general formula (III) is also prepared by a process which comprises the steps of:

reacting a cyclohexanone compound of the aforeindicated general formula (I) with an organometal reagent of the following general formula (11)

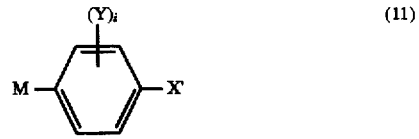
(11)

wherein M represents Li MgU, ZnU or $TiU_k(OW)_{3-k}$ wherein U represents a halogen, preferably Cl, Br or I, or, W represents an alkyl group preferably having from 1 to 6 carbon atoms, and k is zero or an integer of 1 to 3, and X' represents a halogen, preferably Cl, Br or I, and Y represents a halogen, preferably F or Cl, or CH$_3$, and i is a value of 0, 1 or 2, thereby obtaining a compound of the following general formula (12)

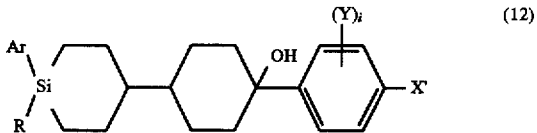

wherein Ar and R have, respectively, the same meanings as defined hereinbefore;

subjecting the compound of the formula (12) to hydrogenolysis or hydrogenation after dehydration to obtain a compound of the following general formula (13)

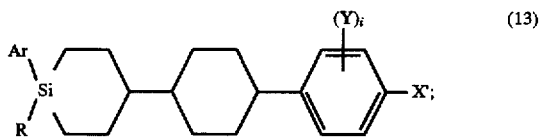

further subjecting the compound of the formula (13) to reaction with an organometal reagent of the following general formula (14)

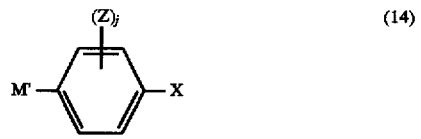

wherein M' represents MgU', ZnU' or TiU'$_k$(OW)$_{3-k}$ in which U' represents a halogen, preferably Cl, Br or I, or B(OV)$_2$ in which V represents H or an alkyl group having preferably 1 to 4 carbon atoms, Z represents a halogen, preferably F or Cl, or CH$_3$ and j is a value of 0, 1 or 2, W and k have, respectively, the same meanings as defined with respect to the formula (11), thereby obtaining a compound of the following general formula (15)

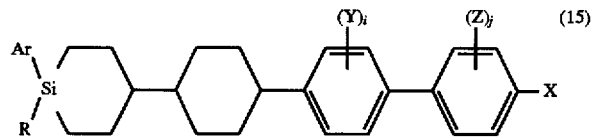

wherein Ar, R, X, Y, Z, i and j have, respectively, the same meanings as defined hereinbefore; and further subjecting the compound of the formula (15) to de-silylation and reduction to obtain a silacyclohexane-based liquid crystal compound of the general formula (III).

DETAILED DESCRIPTION OF EMBODIMENTS
OF THE INVENTION

The embodiments of the invention are described. It will be noted that Ar, R, X, X', Y, Z, i, and j which have, respectively, been defined in the foregoing formulas may not be sometimes defined again in the formulas appearing hereinafter.

According to one embodiment of the invention, a novel cyclohexanone compound of the following general formula (I) is provided

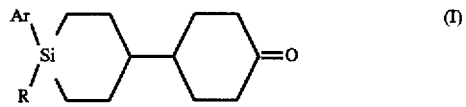

wherein Ar represents a phenyl group or tolyl group, and R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms.

Specific examples of the linear alkyl group having from 1 to 10 carbon atoms represented by R include methyl, ethyl, n-propyl, n-butyl, n-pentyl, n-hexyl, n-heptyl, n-octyl, n-nonyl and n-decyl. Specific examples of the mono or difluoroalkyl group having from 1 to 10 carbon atoms include fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorooctyl, 6-fluorononyl, 6-fluorodecyl, 7-fluoroheptyl, 7-fluorooctyl, 7-fluorononyl, 7-fluorodecyl, 8-fluorocotyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl, 9,9-difluorodecyl and 10,10-difluorodecyl.

Specific examples of the branched alkyl group having 3 to 8 carbon atoms include isopropyl, 1-methylpropyl, 2-methylpropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl and 3-methylheptyl Specific examples of the alkoxyalkyl group having from 2 to 7 carbon atoms include methoxymethyl, ethoxymethyl, propoxymethyl, butoxymethyl, pentoxymethyl, hexyloxymethyl, methoxyethyl, ethoxyethyl, propoxyethyl, butoxyethyl, methoxypropyl, ethoxypropyl, propoxypropyl, butoxypropyl, methoxybutyl, ethoxybutyl, propoxybutyl, methoxypentyl and ethoxypentyl.

Of these, preferred linear alkyl groups are ones having from 3 to 7 carbon atoms and include, for example, n-propyl, n-butyl, n-pentyl, n-hexyl and n-heptyl. Likewise, preferred mono or difluoroalkyl groups include 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoroheptyl, 6-fluorohexyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl and 7,7-difluoroheptyl.

Preferred branched alkyl groups include, for example, isopropyl, 1-methylpentyl, 2-methylpentyl, 1-methylbutyl, 2-methylbutyl, 3-methylbutyl, 1-methylpentyl and 2-ethylhexyl.

Preferred alkoxyalkyl groups include methoxymethyl, methoxyethyl, methoxypropyl, methoxypentyl, ethoxymethyl, ethoxyethyl, propoxymethyl and pentoxymethyl.

The cyclohexanone compound of the formula (I) is prepared from an enamine compound of the following general formula

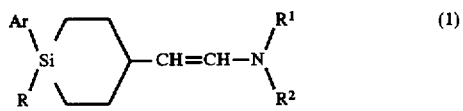

(1)

wherein $R^1$ and $R^2$, respectively, represent an alkyl group having from 1 to 4 carbon atoms or $R^1$ and $R^2$ may join to represent a group of —$(CH_2)_4$—, —$(CH_2)_5$— or —$(CH_2)_2O(CH_2)_2$— thereby completing a cyclic ring along with the nitrogen atom bonded therewith, and methyl vinyl ketone according to the Stork method (G. Stork et al, *J. Amer. Chem. Soc.* 85, 207 (1963)) as will be described in more detail.

The starting enamine compound can be readily prepared from silacyclohexane carbaldehyde compound, which we have already proposed in Japanese Patent Application No. 6-123208, filed May 11, 1994 and assigned to the some assignee.

Typical procedures of preparing enamine compounds are described. In one such procedure, as shown in the following reaction sequence (16), an alkoxymethyltriphenylphosphonium salt is first reacted with a base to obtain a ylide compound, which is then subjected to the Wittig reaction with a silacyclohexane carbaldehyde compound to obtain an alkylenol ether compound, followed by hydrolysis in the presence of an acid catalyst to obtain a silacyclohexane acetaldehyde compound

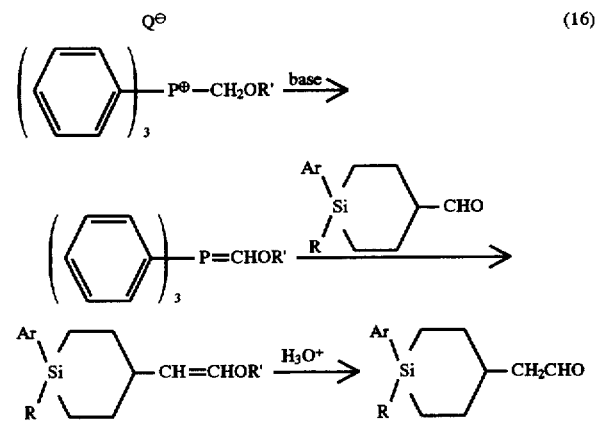

(16)

wherein Ar and R have, respectively the same meanings as defined hereinbefore, R' represents an alkyl group having preferably 1 to 10 carbon atoms and more preferably from 1 to 4 carbon atoms, and Q represents a halogen preferably Cl, Br or I.

The alkoxymethyltriphenylphosphonium salts used in the above reaction include methoxymethyltriphenylphosphonium chloride, methoxymethyltriphenylphosphonium bromide, methoxymethyltriphenylphosphonium iodide, ethoxymethyltriphenylphosphonium chloride, ethoxymethyltriphenylphosphonium bromide, ethoxymethyltriphenylphosphonium iodide and the like.

The bases used for the formation of the ylide compound include organic lithium compounds such as n-butyllithium, s-butyllithium, t-butyllithium, methyllithium, phenyllithium, alkoxides such as sodium methoxide, sodium ethoxide, potassium t-butoxide and the like, and dimsyl sodium.

The reaction between the base and the phosphonium salt is effected in solvents including ethers such as tetrahydrofuran, diethyl ether, di-n-butyl ether, 1,4-dioxane and the like or mixed solvents of the ethers with hydrocarbons such as n-hexane, n-heptane, iso-octane, benzene, toluene, xylene, cumene and the like or aprotic polar solvents such as N,N-dimethylformamide, dimethylsulfoxide, hexamethylphosphoric triamide and the like.

A silacyclohexanecarbaldehyde compound is added to the resultant ylide compound formed in the solvent by which the Wittig reaction is caused to proceed. This reaction may be effected at room temperature although higher or lower temperatures are usable. Preferably, the temperature ranges from 0° C. to a refluxing temperature of solvent used, more preferably from 10° to 40° C. Although the reaction time may differ depending on the types of starting silacyclohexanecarbaldehyde and ylide compound, the reaction time is preferably in the range of 30 minutes to 5 hours.

Then, the resultant alkylenol ether compound is subjected to hydrolysis by an ordinary manner in the presence of an acid catalyst in an amount of 0.1 to 50 wt % based on the ether compound although the amount of the catalyst depends on the types of alkylenol ether and catalyst. Examples of the acid include inorganic acids such as hydrochloric acid, sulfuric acid and the like, and organic acids such as oxalic acid, trifluoroacetic acid, chloroacetic acid and the like.

The silacyclohexanecarbaldehyde obtained in the reaction sequence (16) is subjected to dehydration reaction by use of a secondary amine to obtain an enamine compound. This is shown in the formula (17) below.

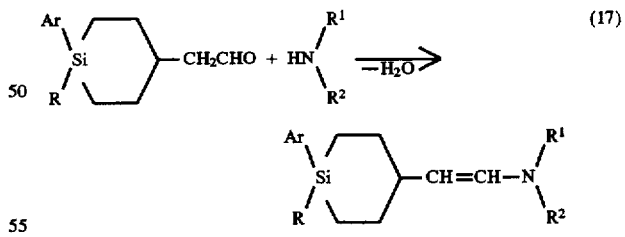

(17)

wherein Ar, R, $R^1$ and $R^2$ have, respectively, the same meanings as defined before.

The use of a hydrocarbon solvent such as benzene, toluene, xylene, cumene n-hexane, n-heptane or the like assists in speeding the reaction wherein the hydrocarbon solvent serves to azeotropically remove the resultant water. For this purpose, the reaction is carried out under refluxing conditions of the solvent. In this case, a catalyst for the dehydration reaction may be used including an add such as p-toluenesulfonic acid, benzenesulfonic acid, camphorsulfonic acid and the like. Although depending on the structure of acetalydehyde and the type of catalyst, the catalyst is preferably used in an amount of from 0.1 to 50 wt % based on the acetaldehyde compound. Alternatively, the formed water may be removed by addition of anhydrous salts such as anhydrous potassium carbonate, anhydrous sodium carbonate and the like. In this case, the reaction is preferably carried out at a temperature ranging from 20 to a refluxing temperature of a solvent used although the temperature does not appear to be critical. The secondary amines used include dimethylamine, diethylamine, di-n-propylamine, pyrrolidine, piperidine, morpholine and the like. The amine is preferably used at a ratio, to the aldehyde compound, by mole of 1:1 to 1:3.

Alternatively, the emanine compounds may be prepared from silacyclohexanone compounds according to the following procedures (A) to (C).

The reaction sequence (A) is shown below.

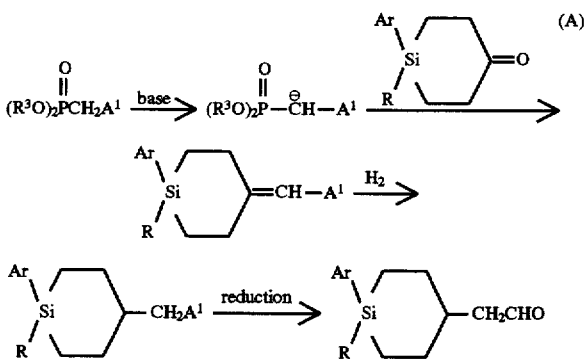

wherein $A^1$ represents CN or $COA^2$ in which $A^2$ represents $OR^4$ or $N(R^5R^6)$ where $R^4$ represents a $C_1$ to $C_6$ alkyl group and $R_5$ and $R_6$ independently represent a $C_1$ to $C_6$ alkyl group, $-(CH_2)_4-$, $-(CH_2)_5-$ or $-(CH_2)_2O(CH_2)_2-$, Ar and R have the same meanings as defined before.

The starting alkylphosphonates include, for example, triethylphosphonoacetate, trimethylphosphonoacetate, methyldiethylphosphonoacetate, diethylcyanomethyl phosphonate, diisopropylcyanomethyl phosphonate and the like. This starting material is reacted with a base as used for the preparation of ylide compounds, e.g. sodium hydride, potassium hydride, lithium hydride and the like.

The resultant compound is then subjected to reaction with a silacyclohexanone compound in a solvent as used for the formation of the ylide compound under reaction conditions of a temperature of 0° to 70° C. and a time of 30 minutes to 5 hours. The resultant unsaturated bond-bearing silacyclohexane compound is hydrogenated at a temperature of from 0° to 150° C. under an atmospheric pressure to 20 kg/cm² of hydrogen in the presence of a catalyst for hydrogenation, e.g. palladium, platinum, rhodium, nickel or ruthenium with or without carbon, barium sulfate, diatomaceous earth. Moreover, the hydrogenated product is reduced under conditions of a temperature of −70° C. to 100° C. in the presence of a reducing agent to silacyclohexanecarbaldehyde as in the formula (A). Examples of the reducing agent include metal halides such as sodium hydride, potassium hydride, trialkylsilanes, boranes, dialkyl aluminium compounds and the like, complex hydrides such as lithium aluminohydride, sodium borohydride, lithium borohydride, potassium borohydride, tributylammonium borohydride and the like, and substituted hydrides thereof such as lithium trialkoxyaluminohydride, sodium di(methoxyethoxy) aluminohydride, lithium triethylborohydride, sodium cyanoborohydride and the like.

The acetaldehyde compound can be converted into an enamine compound in the same manner as with the case using starting silacyclohexane carbaldehyde compounds set out hereinbefore.

Another reaction sequence (B) using silacyclohexanone compounds is shown below.

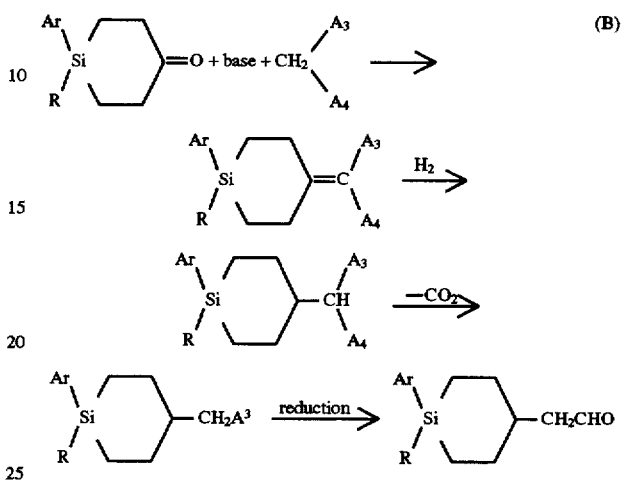

wherein $A^3$ represents CN or $COA^5$ in which $A^5$ is OH, $OR^7$ or $N(R^8R^9)$ wherein $R^7$, $R_8$ and $R_9$ have, respectively, the same meanings are $R_3$ or $R^4$, and $A^4$ represents $COOR^{10}$ wherein $R^{10}$ has the same meaning as $R^3$.

Examples of the compound represented by the formula, $CH_2(A_3A_4)$ include methyl cyanoacetate, ethyl cyanoacetate, cyanoacetic acid, dimethyl malonate, diethyl malonate, ethyl dimethylaminoacetate and the like. The bases are, for example, secondary amines such as piperidine, pyrrolidine, and the like, ammonia and their salts with organic acids. Examples of the organic acid include carboxylic acids such as formic acid, acetic acid, propionic acid, benzoic acid and the like. In addition, there may be used organolithium compounds such as n-butyllithium, s-butyllithium, t-butyllithium, methyllithium phenyllithium and the like, alkoxides such as sodium methoxide, sodium ethoxide, potassium t-butoxide and the like, and dimsyl sodium.

The first step of the sequence (B) is usually effected at a temperature of from 60° to 150° C., preferably from 80° to 140° C., while distilling off secondarily produced water.

The resultant product is then hydrogenated in a manner similar to the case of the sequence (A), followed by decarboxylation. The decarboxylation is effected by adding an inorganic acid such as hydrochloric acid, sulfuric acid or the like or metal salts thereof such as Li, Na or K salts and water in an amount not less than an equivalent to the product to be decarboxylated in a solvent. Examples of the solvent include aromatic hydrocarbons and aromatic ethers such as toluene, xylene, cumene, diethylbenzene, phenetole and the like, and high boiling aprotic polar solvents such as dimethylformamide, dimethylacetamide, dimethylimidazolidinone, dimethylurea, dimethylsulfoxide, hexamethylphosphoric triamide and the like. The decarboxylation reaction is carried out under conditions of a temperature of 100° to 200° C. for a time of 2 to 12 hours. The reduction is performed as in the sequence (A). By this, the acetaldehyde compound is obtained and can be converted into an enamine compound set out hereinbefore.

A further reaction sequence of preparing the acetaldehyde compound is shown below.

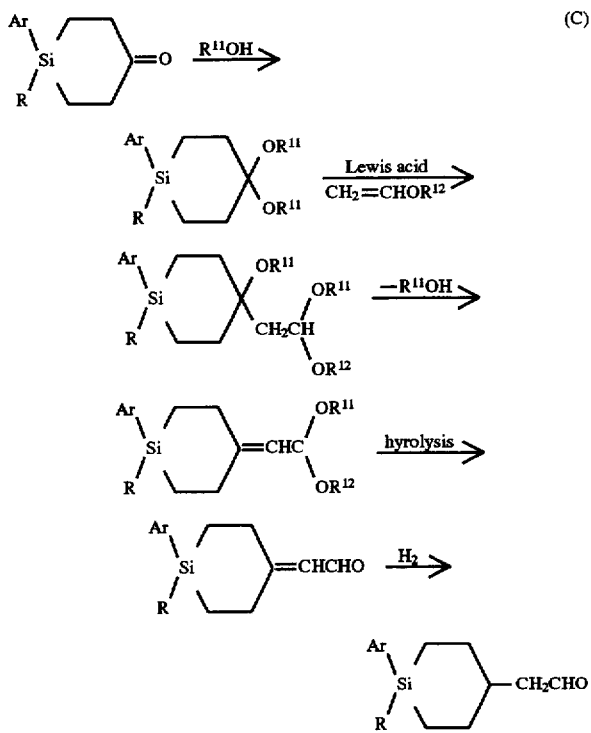

wherein $R^{11}$ has the same meaning as $R^3$ or is —$(CH_2)_2$—, —$(CH_2)_3$— or —$(CH_2)_4$— with or without a substituent and $R^{12}$ has the same meaning as $R^3$.

In the sequence (C), the silacyclohexanone is reacted with an alcohol. Examples of the alcohol include monohydric alcohols having from 1 to 6 carbon atoms or dihydric alcohols such as HO—$(CH_2)_2$—OH, HO—$(CH_2)_3$—OH, HO—$(CH_2C(CH_3)_2CH_2)$—OH, HO—$(CH_2)_4$—OH and the like.

The reaction is effected in the presence of an acid for dehydration. Examples of the acid include inorganic acids such as hydrochloric acid, sulfuric acid, nitric acid and the like, and salts thereof, and organic acids such as p-toluenesulfonic acid, camphorsulfonic acid, trifluoroacetic acid and the like. In order to quickly remove the secondarily produced water, hydrocarbons such as benzene, toluene, xylene, cumene, hexane, iso-octane and the like are used as a solvent, in which the reaction is caused to proceed azeotropically.

Thereafter, the resultant product is reacted with an alkyl vinyl ether in the presence of a Lewis acid under conditions of $-50°$ to $100°$ C., preferably from $-30°$ to $50°$ C. This reaction proceeds in a solvent or in the absence of any solvent. If used, the solvent includes, for example, halogenated hydrocarbons such as methylene chloride, chloroform and the like. The Lewis acids include, for example, $AlX_3^+$, $ZnX_2^+$, $MgX_2^+$, $FeX_2^+$, $BF_3$ and the like wherein $X^+$ halogen. The alkyl vinyl ethers include ethyl vinyl ether, butyl vinyl ether and the like.

Subsequently, hydrolysis is effected by a usual manner as in the case using the carbaldehyde, followed by hydrogenation or reduced as in the sequence (A), thereby obtaining the acetaldehyde. The acetaldehyde can be readily converted into an enamine compound.

In accordance with the present invention, the thus prepared enamine compound is used as one of the starting materials and subjected to Michael reaction with methyl vinyl ketone according to the following reaction formula (18)

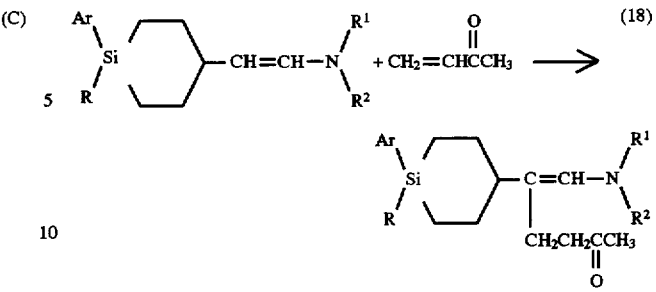

The reaction is carried out at a ratio by equivalent between the enamine compound and methyl vinyl ketone of 1:1 to 5:1, preferably 1:1 to 1.5:1, in a solvent under heating conditions preferably including a temperature, depending on the structure of enamine, ranging from $0°$ to $150°$ C., more preferably under refluxing for a time sufficient to complete the reaction, e.g. several tens of minutes to several tens of hours depending on the temperature used. The solvents include, for example, hydrocarbons such as benzene, toluene, xylene, cumene, n-hexane, n-heptane, iso-octane, cyclohexane and the like, ethers such as tetrahydrofuran, diethyl ether, di-n-butylether, 1,4-dioxane and the like, alcohols such as methanol, ethanol, propanol, butanol and the like, polar solvents such as N,N-diemthylformamide, dimethylsulfoxide, hexamethylphosphoric triamide, 1,3-dimethyl-2-imidazolidinone, N,N'-dimethylpropylene urea and the like. These solvents may be used singly or in combination. If a protic solvent such as methanol, ethanol or the like is added, the Michael reaction may proceed within a shorter time owing to the acceleration of movement of protons in the reaction.

The resultant Michael adduct may be then subjected to intramolecular aldol condensation as it is, thereby obtaining a cyclohexenone compound. Alternatively, the adduct may be hydrolyzed with the aid of an inorganic acid such as hydrochloric acid, sulfuric acid or the like or an organic acid such as oxalic acid, trifluoroacetic acid, chloroacetic acid or the like to obtain an aldehyde compound of the formula (19), followed by intramolecular aldol condensation to obtain a cyclohexenone compound

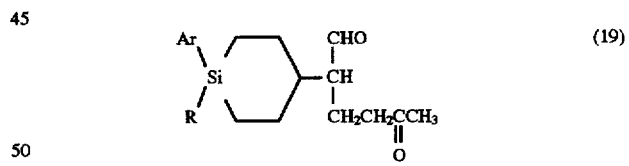

The intramolecular aldol condensation reaction is shown in the following reaction formula (20)

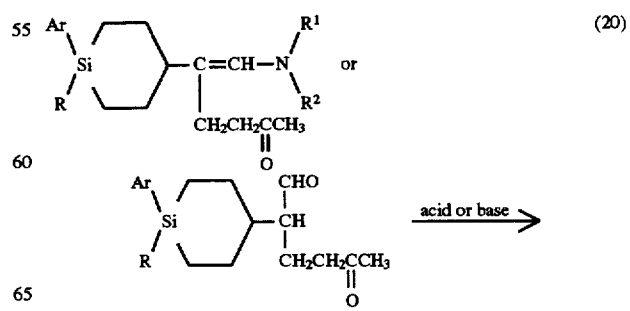

-continued

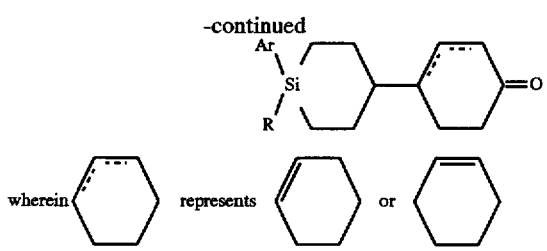

The aldol condensation reaction proceeds in the presence of a base or acid catalyst. The catalyst may be added freshly. It should be noted that the secondary amine for the enamine compound used in the preceding Michael addition reaction has the catalytic function and the aldol condensation reaction may proceed without fresh addition of any fresh catalytic compound. Although this aldol condensation reaction may proceed at room temperature, a temperature ranging from room temperature to a refluxing temperature of a solvent used is preferred in the practice of the invention.

If present, the base catalysts include, for example, organic bases such as the secondary amines set out hereinbefore, triethylamine, tri-n-butylamine, dimethylaniline and the like, inorganic bases such as sodium carbonate, potassium carbonate, sodium hydrogencarbonate, potassium hydrogencarbonate and the like, and alkoxides such as sodium methoxide, sodium ethoxide, potassium t-butoxide and the like. Examples of the acid catalyst include inorganic acid such as hydrochloric acid, sulfuric acid and the like, and organic adds such as p-toluenesulfonic add, benzenesulfonic acid, acetic add, propionic acid, oxalic acid, trifluoroacetic add, chloroacetic acid and the like. These bases or adds may be used singly or in combination and are properly used taking into consideration the structure of the ketoaldehyde or the types of groups represented by Ar and R in the ketoaldehyde. The base or acid is preferably used in an amount of 0.1 to 50 wt % based on the starting material, which may depend on the structure of the ketoaldehyde.

During the course of the aldol condensation reaction in the presence of a base catalyst, if once produced cyclohexenone compound is further reacted and converted into an enamine compound of the cyclohexenone, i.e. a compound of the following general formula (21)

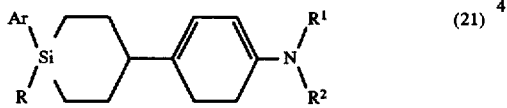 (21)

wherein Ar, R, $R^1$ and $R^2$ have, respectively, the same meanings as defined hereinbefore, or if the aldol condensation reaction stops at the stage where a β-hydroxyketone compound of the following general formula (22) is predominantly formed

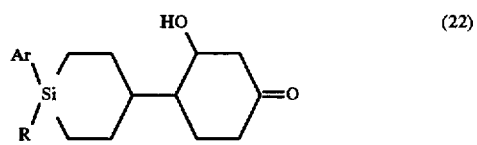 (22)

the cyclohexenone compound of the formula (20) can be obtained by treatment with an acid of the type as set out hereinabove.

The cyclohexenone compound is then subjected to catalytic reduction or hydrogenation at the double bond thereof to obtain a cyclohexanone compound of the general formula (I) of the present invention. This is particularly shown in the following reaction formula (23)

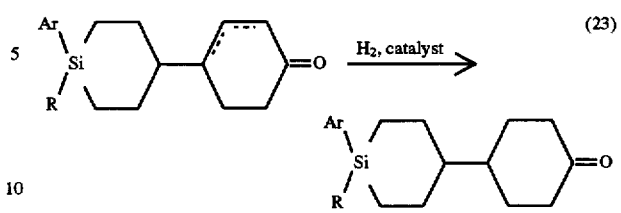 (23)

The temperature for the hydrogenation depends on the structure of the cyclohexanone and is not critical. Preferably, the temperature is in the range of from 0° to 150° C., more preferably from 20° to 100° C. Although a higher pressure of hydrogen results in a higher reaction velocity for the same catalyst, limitation may be placed on the type of apparatus used and the pressure is preferably in the range of from an atmospheric pressure to 20 kg/cm$^2$.

The catalysts for the hydrogenation include, for example, metals such as palladium, platinum, rhodium, nickel, ruthenium and the like. Better results are obtained using palladium-carbon, palladium-barium sulfate, palladium-diatomaceous earth, platinum oxide, platinum-carbon, rhodium-carbon, Raney nickel and the like. In order to increase the reaction velocity, co-catalysts such as trifluoroacetic acid, perchloric acid and the like may be further added.

The cyclohexanone compound of the general formula (I) obtained in such a manner as set forth hereinabove is used to prepare various types of silacyclohexane-based liquid crystal compounds. The preparation of the derivatives of the cyclohexanone compound is described.

First, an organometallic reagent readily prepared from a corresponding halide compound is reacted with the cyclohexanone compound, whereupon an alcohol compound is obtained as shown in the following reaction formula (24)

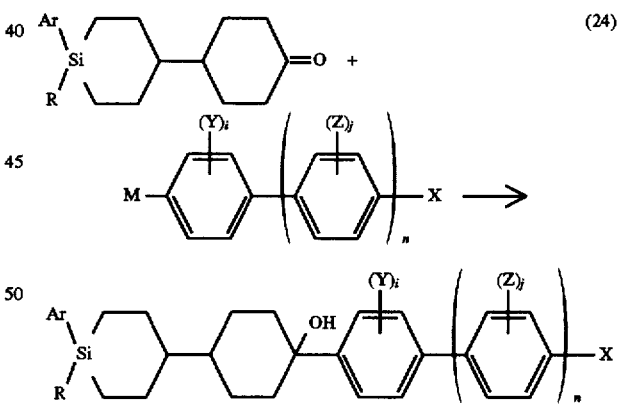 (24)

wherein Ar, R, M, X, Y, Z, i and j have, respectively, the same meanings as defined hereinbefore, and n is a value of 0 or 1.

The organometallic reagents include Grignard reagents, organozinc reagents, organolithium reagents, organotitanium reagents and the like. Using any of these reagents, the reaction proceeds in high yield. The reaction conditions are not critical and may depend on the type of ketone and the structure of an organometal used and preferably include a temperature of from −70° to 150° C. and a time of from 30 minutes to 5 hours. The reaction is usually effected in a solvent. Examples of the solvent include ethers such as diethyl ether, tetrahydrofuran, dioxane and the like, hydrocarbons such as benzene, toluene, xylene, mesitylene, hexane, heptane octane and the like, or mixtures thereof.

Thereafter, the alcohol compound is converted to a cyclohexanone compound either by hydrogenolysis or by dehydration reaction in the presence of an acid catalyst and then hydrogenation of the resultant double bond according to the following reaction formula example, inorganic acids such as hydrochloric acid, sulfuric acid, nitric acid, perchloric acid and the like and salts thereof, and organic acids such as p-toluenesulfonic acid, camphorsulfonic acid, trifluoroacetic acid and the like. In order to quickly remove the resultant water, hydrocarbons may be used as a solvent, including benzene, toluene,

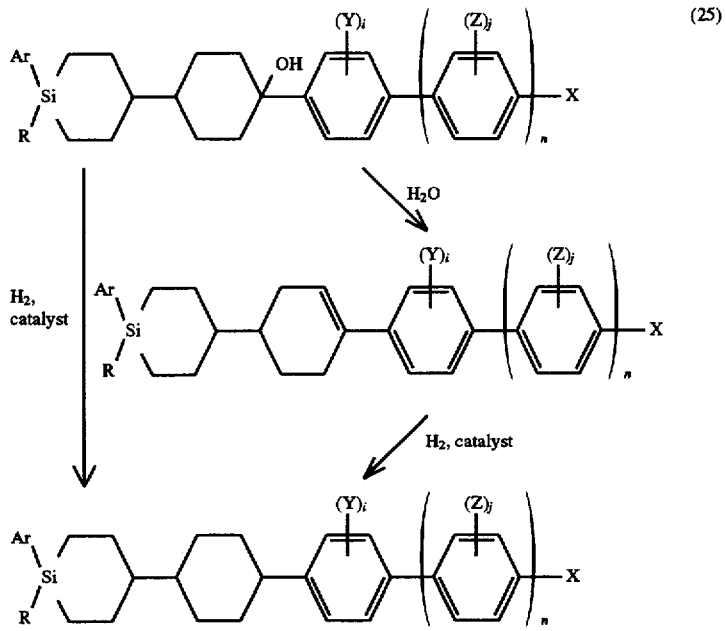

(25)

The reaction conditions vary depending on the structure of the alcohol. The hydrogenolysis effectively proceeds in the presence of a catalyst, preferably, under conditions of a temperature range from 0° to 150° C., more preferably from 20° to 100° C. and a pressure of hydrogen ranging from an atmospheric pressure to 20 kg/cm² although a lower or higher pressure may be used. A lower pressure resets in a lower reaction velocity and a higher pressure will require a more expensive apparatus. Accordingly, the reaction conditions and the type of reactor should properly be used to effect the reaction under economical conditions. Examples of the catalyst include metals such as palladium, platinum, rhodium, nickel, ruthenium and the like. Better results are obtained using palladium-carbon, palladium-barium sulfate, palladium-diatomaceous earth, platinum oxide, platinum-carbon, rhodium-carbon, Raney nickel, palladium oxide, Ni-diatomaceous earth and the like. Of these, it is more preferred to use Ni and Pd-based catalysts.

Alternatively, the alcohol compound may be first dehydrated in the presence of an acid catalyst by a usual manner. The acids used for the dehydration reaction include, for xylene, cumene, hexane, iso-octane and the like. These hydrocarbons assist in speeding the reaction through azeotropy.

The resultant double bond is then hydrogenated in the presence of a catalyst as defined with respect to the hydrogenolysis to provide a cyclohexanone compound. The hydrogenation is preferably effected in the same manner as in the hydrogenation reaction set out with respect to the formula (23). It will be noted that a higher reaction velocity and a high pressure of hydrogen require a more expensive reactor. In this sense, the reactions set out hereinbefore should be so controlled that they are conducted under conditions as economical as possible while taking the types or structures of reactants used in the respective steps.

Subsequently, the cyclohexanone compound is subjected to de-silylation reaction with a electrophilic reagent to provide a halosilacyclohexane compound, followed by reduction reaction to obtain a silacyclohexane-based liquid crystal compound. This is particularly shown in the following reaction sequence (26)

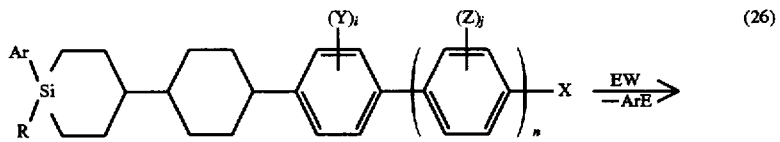

(26)

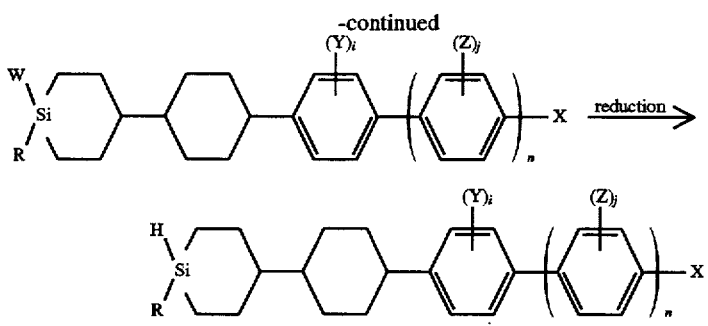

wherein EW represents an electrophilic reagent, and W represents a halogen and preferably Cl, I or Br.

The electrophilic reagents include, for example, halogens, hydrogen halides, meal halides, sulfonic derivatives, acid halides, alkyl halides and the like. Preferable examples include iodine, bromine, chlorine, iodine monochloride, hydrogen chloride, hydrogen bromide, hydrogen iodide, mercury (II) halide, trimethylsilyl chlorosulfonate, acetyl chloride, acetyl bromide, benzoyl chloride, t-butyl chloride and the like. In order to increase the reaction velocity, addition of Lewis acids such as aluminum chloride, zinc chloride, titanium tetrachloride, boron trifluoride and the like or irradiation of visible light or UV light is effective. The de-silylation reaction may be effected in a wide range of temperature. The reaction temperature is preferably in the range of from 0° to 80° C., more preferably from 10° to 40° C. The electrophilic reagent is preferably used at a ratio by mole between the cyclohexanone compound and the electrophilic reagent of 1:1 to 1:5, more preferably 1:1 to 1:2.

The reagents used for the reduction of the resultant halosilacyclohexane compound include, for example, metal halides such as sodium hydride, potassium hydride, trialkylsilanes, boranes, dialkyl aluminium compounds and the like, complex hydrides such as lithium aluminohydride, sodium borohydride, lithium borohydride, potassium borohydride, tributylammonium borohydride and the like, and substituted hydrides thereof such as lithium trialkoxyaluminohydride, sodium di(methoxyethoxy) aluminohydride, lithium triethylborohydride, sodium cyanoborohydride and the like.

Although not limitative, the reduction of the halosilacyclohexane is carried out preferably at a temperature of from 0° to 150° C., more preferably from 20° to 100° C.

By the above process, a silacyclohexane-based liquid crystal compound can be prepared. This compound may be used as a liquid crystal as it is or after separation into a trans form of the compound by a usual manner such as chromatography.

Among the products obtained according to the aforeindicated reaction formula (25), a compound of the following formula (27), corresponding to a final compound of the formula (25) wherein n=0,

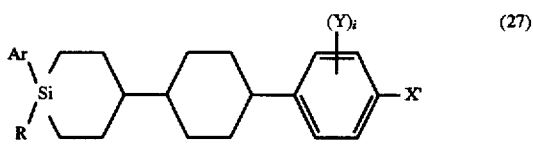

wherein Ar, R, Y and i have, respectively, the same meanings as defined hereinbefore and X' represents a halogen preferably including Cl, Br or I, is used to prepare a compound of the following general formula (28) which corresponds to the final compound of the general formula (25) wherein n=1

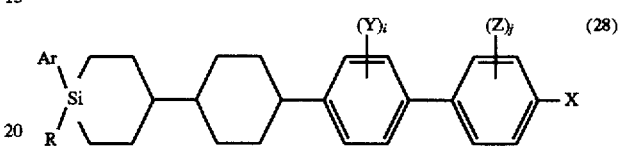

The above reaction proceeds according to the following reaction formula (29)

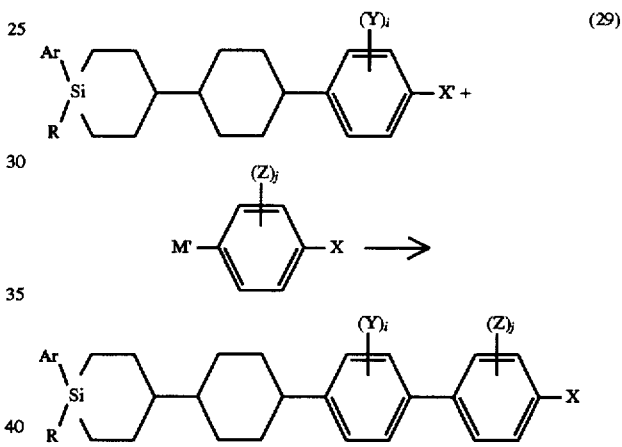

wherein M' represents MgU, ZnU or TiU$_k$(OW)$_{3-k}$ wherein U represents a halogen and preferably Cl, Br or I, or B(OV) wherein V represents a hydrogen atom or an alkyl group preferably having from 1 to 4 carbon atoms, W represents an alkyl group preferably having from 1 to 6 carbon atoms, and k is zero or an integer of 1 to 3.

This reaction is effected in the presence of a catalyst of a transition metal compound. Preferred examples of the catalyst include palladium or nickel compounds. The palladium catalysts include, for example, zero valent palladium compounds such as tetrakis(triphenylphosphine)palladium (0), di-[1,2-bis(diphenylphosphino)ethane]palladium (0) and the like, compounds consisting of divalent palladium compounds, such as palladium acetate, palladium chloride, [1,1-bis(diphenylphosphino)ferrocene]palladium (II) chloride and the like, and combinations of those compounds mentioned above with reducing agents.

Examples of the nickel catalyst include divalent nickel compounds such as 1,3-bis (diphenylphosphino)propane nickel (II) chloride, 1,2-bis(diphenylphosphino)ethane nickel (II) chloride, bis(triphenylphosphine) nickel (II) chloride and the like, zero valent nickel compounds such as tetrakis(triphenylphosphine) nickel (0) and the like.

If the organometallic compound used is a boric acid derivative wherein M represents B(OV)$_2$, it is preferred that the reaction is carried out in the presence of a base.

Examples of the base include inorganic bases such as sodium carbonate, sodium hydrogencarbonate, potassium carbonate, sodium hydroxide, sodium hydrogencarbonate, potassium carbonate, sodium hydroxide, potassium hydroxide and the like, and organic bases such as triethylamine, tributylamine, dimethylaniline and the like. The reaction of the formula (29) is preferably effected at a temperature ranging from 0° to 150° C., more preferably from 20° to 120° C.

The compound obtained according to the reaction formula (29) can be converted into a silacyclohexane-based liquid crystal compound according to the reaction sequence (26) indicated before.

The thus prepared compounds may be purified by a usual manner such as recrystallization, chromatography or the like, thereby obtaining silacyclohexane-based liquid crystal compounds in an intended trans form, if necessary.

It will be noted that in the processes set out hereinbefore, the respective steps except the hydrogenolysis or hydrogenation step do not seem to be critical with respect to the reaction temperature, reaction time and other reaction conditions although preferred ranges of the temperature in the respective steps are set forth. Higher temperatures usually result in a higher reaction velocity but additional heating energy is required. Higher or lower pressure may be used but normal pressures are suitably used. The reactions in the respective steps may fundamentally proceed stoichiometrically. Anyway, operating conditions of the reactions in the respective steps especially, the temperature and the time, are interrelated, i.e. a higher temperature leads to a shorter reaction time.

The present invention is more particularly described by way of examples.

EXAMPLE 1

Preparation of 4-(4-phenyl-4-n-propyl-4-silacyclohexyl) cyclohexanone 246 g of 4-phenyl-4-n-propyl-4-silacyclohexanecarbaldehyde was dropped in a ylide solution which had been prepared from 350 g of methoxymethyltriphenylphosphonium chloride and 130 g of potassium t-butoxide in 800 ml of tetrahydrofuran. After agitation at room temperature for 2 hours, the reaction mixture was poured into water, followed by extraction with ether. The ether phase was washed with brine, dried and concentrated to obtain a residue, to which n-hexane was added. The resultant crystals of triphenylphosphine oxide were separated by filtration and the resultant filtrate was concentrated to obtain a crude methyl ether. This ether was dissolved in methylene chloride, to which 20% hydrochloric acid was added, followed by agitation at room temperature for 5 hours. The resultant methylene chloride phase was washed with brine, dried and concentrated, followed by purification through silica gel chromatography to obtain 255 g (yield: 98%) of 4-phenyl-4-n-propyl-4-silacyclohexanecarbaldehyde.

The thus obtained product was subjected to IR analysis with the results shown below.

IR (liquid film) vmax: 2920, 1720, 1105, 695 cm$^{-1}$

A mixture of 255 g of the acetaldehyde product, 75 g of pyrrolidine and 800 ml of benzene was refluxed during which the resultant water was removed. When distilling of water ceased, a mixture of 80 g of methyl vinyl ketone and 200 ml of methanol was added to the reaction system, followed by agitation at room temperature for 48 hours. Subsequently, 100 ml of acetic acid, 50 g of sodium acetate and 100 ml of water were added to the reaction mixture, followed by agitation for a further 4 hours. The resultant reaction mixture was subjected to extraction with benzene, washed with brine, dried and concentrated, followed by purification through silica gel chromatography to obtain 164 g of 4-(4-phenyl-4-n-propyl-4-silacyclohexyl)-2-cyclohexenone ($\alpha,\beta$-unsaturated ketone) and 70 g of 4-(4-phenyl-4-n-propyl-4-silacyclohexyl)-3-cyclohexenone ($\beta,\gamma$-unsaturated ketone) (yield of both cyclohexenones: 76%).

The results of IR analysis are shown below. IR (liquid film) $v_{max}$ ($\alpha,\beta$-unsaturated ketone): 2920, 1675, 1105, 695 cm$^{-1}$ IR (liquid film) $v_{max}$ ($\beta,\gamma$-unsaturated ketone): 2920, 1715, 1105, 700 cm$^{-1}$ The mixture of both unsaturated ketones was dissolved in 300 ml of ethanol and subjected to hydrogenation in the presence of 2.0 g of palladium-carbon at a pressure of 10 kg/cm$^2$ of hydrogen. When hydrogen was consumed in a theoretical amount, the catalyst was removed by filtration and concentrated under reduced pressure to obtain 234 g (yield: 99%) of the intended product.

The thus obtained product was subjected to IR, GS-MS and NMR analyses with the results shown below.

1H-NMR (CDCl$_3$) δ: 0.50 to 2.60 (25H, m), 7.25 to 7.65 (5H,m) ppm

GS-MS (70 eV) (m/z)$^+$: 105, 123, 208, 236, 271, 314

IR (liquid film) $v_{max}$: 2920, 1710, 1425, 1105, 700 cm$^{-1}$

EXAMPLE 2

Preparation of 4-[4-(3-methylbutyl)-4-phenyl-4-silacyclohexyl)cyclohexanone

The general procedure of Example 1 was repeated except that 4-(3-methylbutyl)-4-phenyl-4-silacyclohexanecarbaldehyde was used instead of 4-phenyl-4-n-propyl-4-silacyclohexanecarbaldehyde, thereby obtaining the captioned compound.

EXAMPLE 3

Preparation of 4-(4,4-diphenyl-4-silacyclohexyl) cyclohexanone

In the same manner as in Example 1, 29.4 g (yield: 93%) of 4,4-diphenyl-4-silacyclohexyl aldehyde was obtained from 30.0 g of 4,4-diphenyl-4-silacyclohexanecarbaldehyde. The results of IR analysis of this aldehyde are shown below IR (liquid film) $v_{max}$: 3060, 2920, 1710, 1425, 1110, 725, 695 cm$^{-1}$ While a mixture of 29.4 g of the aldehyde compound, 8.6 g of piperidine and 100 ml of benzene was refluxed, the resultant water was removed. When distilling of water ceased, 7.5 g of methyl vinyl ketone and 100 ml of 1,4-dioxane were added, followed by agitation at 40° C. for 2 hours. 200 ml of 20% hydrochloric acid was added to the reaction mixture, followed by refluxing for 2 hours. Thereafter, the resultant organic phase was washed with brine, dried and concentrated to obtain 32.4 g (yield: 89%) of $\alpha$-(4,4-diphenyl-4-silacyclohexyl)-$\alpha$-(3-ketobutyl) acetaldehyde. The results of IR and GS-MS analyses of the product are shown below.

IR (liquid film) $v_{max}$: 3060, 2920, 1715, 1425, 1105, 725, 700 cm$^{-1}$

GS-MS (70 eV) (m/z)$^+$: 43, 105, 183, 199, 287, 307, 364

32.4 g of the acetaldehyde was dissolved in 100 ml of ethanol, to which 0.5 g of sodium ethoxide was added, followed by refluxing for 2 hours, pouring into 20% hydrochloric acid and extraction with ethyl acetate. The ethyl acetate solution was washed with brine, dried and concentrated, followed by purification through silica gel chromatography to obtain 18.0 g of 4-(4,4-diphenyl-4-silacyclohexyl)-2-cyclohexenone (α,β-unsatured ketone) and 12.2 g of 4-(4,4-diphenyl-4-silacyclohexyl)-3-cyclohexenone (β,γ-unsaturated ketone) (yield of both cyclohexenones: 97%).

The results of IR analysis are shown below.

IR (liquid film) $v_{max}$ (α,β-unsaturated ketone): 3060, 2920, 1680, 1415, 1110, 725, 700 $cm^{-1}$ IR (liquid film) $v_{max}$ (β,γ-unsaturated ketone): 3060, 2920, 1705, 1420, 1105, 725, 700 $cm^{-1}$ The mixture of both unsaturated ketones was hydrogenated in the same manner as in Example 1 to obtain 29.9 g (yield: 99%) of the intended product.

The thus obtained product was subjected to IR and NMR analyses along with the measurement of a melting point, with the results shown below. $^1$H-NMR (CDCl$_3$) δ: 0.80–2.50 (18H, m), 7.20–7.70 (10H, m) ppm IR (KBr disc) $v_{max}$: 3050, 2920, 1710, 1415, 1110, 980, 705 $cm^{-1}$ Melting point: 92.1° C.

EXAMPLE 4

Preparation of 4-(4-n-pentyl-4-phenyl-4-silacyclohexyl) cyclohexanone

The general procedure of Example 3 was repeated except that 4-(4-n-pentyl-4-phenyl-4-silacyclohexane) carbaldehyde was used, thereby obtaining the intended product. The product was subjected to IR and NMR analyses with the following results.

$^1$H-NMR (CDCl$_3$) δ: 0.50–2.50 (29H, m), 7.20–7.65 (5H,m) ppm

IR (liquid film) $v_{max}$: 2920, 1715, 1415, 1105, 700 $cm^{-1}$

EXAMPLE 5

Preparation of 4-(4-(4-pentenyl)-4-phenyl-4-silacyclohexyl) cyclohexanone

The general procedure of Example 3 was repeated except that 4-(4-(4-pentenyl)-4-phenyl-4-silacyclohexane) carbaldehyde was used, thereby obtaining the intended product.

EXAMPLE 6

Preparation of trans, trans-4-(4-(4-fluorophenyl)cyclohexyl)-1-n-propyl-1-silacyclohexane 31.5 g of 4-(4-phenyl-4-n-propyl-4-silacyclohexyl) cyclohexanone was dropped in 120 ml of a solution of 1.0 mole of p-fluorophenylmagnesium chloride in tetrahydrofuran at a temperature of 40° to 50° C. After agitation at 50° C. for 2 hours, the reaction mixture was poured into a saturated ammonium chloride aqueous solution, followed by extraction with benzene. 1.0 g of p-toluenesulfonic acid monohydrate was added to the benzene phase, followed by distilling off the resultant water under reflux. When the distilling of water stopped, the benzene solution was washed with a sodium hydrogencarbonate aqueous solution, dried and concentrated to obtain crude 4-(4-(4-fluorophenyl)-3-cyclohexenyl)-1-phenyl-1-n-propyl-1-silacyclohexane. This product was dissolved in 100 ml of ethanol and hydrogenated in the presence of 1.0 g of a palladium-carbon catalyst, followed by separation of the catalyst by filtration and concentration to obtain 35.0 g (yield: 88%) of 4-(4-(4-fluorophenyl)cyclohexyl)-1-phenyl-1-n-propyl-1-silacyclohexane. The results of IR analysis are shown below.

IR (liquid film) $v_{max}$: 2920, 2860, 1510, 1225, 1110, 825, 695 $cm^{-1}$ 100 ml of a carbon tetrachloride solution of 1.0 mole of iodine monochloride was added to 35.0 g of the product at room temperature, followed by agitation for 30 minutes and concentration. The resultant residue was dissolved in 100 ml of tetrahydrofuran and dropped in a mixture of 4.0 g of lithium aluminohydride and 50 ml of tetrahydrofuran at 0° C. The reaction mixture was agitated for 1 hour, after which it was poured into 200 ml of 5% hydrochloric acid, followed by extraction with ethyl acetate. The resultant extract was subjected to ordinary washing with brine, drying and concentration, followed by purification through silica gel chromatography to obtain 15.2 g (yield: 54%) of the intended product. The product was subjected to NMR and IR analyses with the results shown below.

$^{13}$C-NMR (CDCl$_3$) δ: 10.14 (s), 14.78 (s), 17.81 (s), 17.95 (s), 28.63 (s), 29.95 (s), 34.85 (s), 43.60 (s), 43.93 (s), 45.89 (s), 114.86 (d), 128.00 (d), 143.38 (s), 161.12 (d) ppm IR (KBr disc) $v_{max}$: 2918, 2848, 2104, 1605, 1510, 1448, 1227, 1159, 985, 887 $cm^{-1}$

EXAMPLE 7

Preparation of trans, trans-4-(4-(4-chloro-3-fluorophenyl) cyclohexyl)-1-n-pentyl- 1-silacyclohexane The general procedure of Example 6 was repeated using 4-(4-phenyl-4-pentyl-4-silacyclohexyl)cyclohexanone and 4-chloro-3-fluorophenylmagnesium chloride, thereby obtaining trans, trans-4-(4-(4-chloro-3-fluorophenyl) cyclohexyl-1-n-pentyl-1-silacyclohexane. The results of GS-MS analysis are shown below.

GS-MS (70 eV) (m/z)$^+$: 71, 99, 143, 187, 269, 309, 345, 380

EXAMPLE 8

Preparation of trans, trans-4-(4-(4-fluorophenyl)cyclohexyl)-1-n-pentyl-1-silacyclohexane The general procedure of Example 6 was repeated using 4-(4-phenyl-4-pentyl-4-silacyclohexyl)cyclohexanone and p-fluorophenylmagnesium chloride, thereby obtaining trans, trans-4-(4-(4-fluorophenyl)cyclohexyl)-1-n-pentyl-1-silacyclohexane. The results of NMR and IR analyses are shown below.

$^{13}$C-NMR (CDCl$^3$) δ: 10.12 (s), 12.19 (s), 14.01 (s), 22.37 (s), 24.13 (s), 28.63 (s), 29.95 (s), 34.86 (s), 35.41 (s), 43.60 (s), 43.94 (s), 45.91 (s), 114.86 (d), 128.00 (d), 143.37 (d), 161.12 (d) ppm IR (KBr disc) $v_{max}$: 2918, 2848, 2100, 1603, 1510, 1227, 987, 885 $cm^{-1}$

EXAMPLE 9

Preparation of trans, trans-4-(4-(3,4-difluorophenyl) cyclohexyl)-1-n-propyl-1-silacyclohexane The general procedure of Example 6 was repeated using 4-(4-phenyl-4-n-propyl-4-silacyclohexyl)cyclohexanone and 3,4-difluorophenylmagnesium bromide, thereby obtaining trans, trans-4-(4-(3,4-difluorophenyl)cyclohexyl-1-n-propyl-1-silacyclohexane. The results of NMR and IR analyses are shown below.

$^1$H-NMR (CDCl$_3$) δ: 8:0.38–0.62 (2H, m), 0.84–1.43 (15H, m), 1.66–1.76 (2H, m 1.80–1.95 (4H, m), 2.38 (1H, tt), 3.66–3.76 (1H, m), 6.83–7.09 (3H, m) p IR (KBr disc) $v_{max}$: 2924, 2854, 2100, 1606, 1518, 1279, 987, 887 $cm^{-1}$

EXAMPLE 10

Preparation of trans, trans-4-(4-(3,4-difluorophenyl) cyclohexyl)-1-(3-methylbutyl)-1-silacyclohexane The general procedure of Example 6 was repeated using 4-(4-phenyl-4-(methylbutyl)-4-silacyclohexyl) cyclohexanone and 3,4-difluorophenylmagnesium chloride, thereby obtaining trans, trans-4-(4-(3,4-difluorophenyl) cyclohexyl-1-(3-methylbutyl)-1-silacyclohexane. The results of NMR and IR analyses are shown below.

$^{13}$C-NMR (CDCl$_3$) δ: 9.70 (s), 10.01 (s), 22.12 (s), 28.60 (s), 29.80 (s), 30.70 (s), 33.48 (s), 34.65 (s), 43.52 (s), 43.89 (s), 45.84 (s), 115.38 (d), 116.71 (d), 124.45 (dd), 144.79 (dd), 148.52 (dd), 150.16 (dd) ppm IR (liquid film) $v_{max}$: 2922, 2852, 2100, 1608, 1518, 1279, 1207, 987, 889 cm$^{-1}$

EXAMPLE 11

Preparation of trans, trans-4-(4-(3,4-difluorophenyl) cyclohexyl)-1-(4-pentenyl)-1-silacyclohexane The general procedure of Example 6 was repeated using 4-(4-phenyl-4-(pentenyl)-4-silacyclohexyl)cyclohexanone and 3,4-difluorophenylmagnesium bromide, thereby obtaining trans, trans-4-(4-(3,4-difluorophenyl)cyclohexyl)-1-(4-pentenyl)-1-silacyclohexane. The results of NMR and IR analyses are shown below.

$^{13}$C-NMR (CDCl$_3$)δ: 10.01 (s), 11.73 (s), 23.89 (s), 28.56 (s), 29.77 (s), 34.61 (s), 37.16 (s), 43.50 (s), 43.83 (s), 45.80 (s), 114.54 (s), 115.30 (d), 116.66 (d), 122.39 (dd), 138.57 (s), 144.70 (dd), 148.49 (dd), 150.13 (dd) ppm IR (liquid film) $v_{max}$: 2922, 2852, 2100, 1606, 1518, 1279, 1117, 887, 818 cm$^{-1}$

EXAMPLE 12

Preparation of trans, trans-4-(4-(3,4-difluorophenyl) cyclohexyl)-1-n-pentyl-1-silacyclohexane The general procedure of Example 6 was repeated using 4-(4-phenyl-4-(pentyl)-4-silacyclohexyl)cyclohexanone and 3,4-difluorophenylmagnesinm bromide, thereby obtaining trans, trans-4-(4-(3,4-difluorophenyl)cyclohexyl)-1-n-pentyl)-1-silacyclohexane. The results of NMR and IR analyses are shown below.

$^{13}$C-NMR (CDCl$_3$) δ: 9.70 (s), 10.11 (s), 12.17 (s), 13.99 (s), 22.38 (s), 24.14 (s), 28.62 (s), 29.80 (s), 34.65 (s), 35.43 (s), 43.55 (s), 43.89 (s), 45.86 (s), 115.36 (d), 116.70 (d), 122.42 (s), 144.78 (s), 148.43 (dd), 150.17 (dd) ppm IR (KBr disc) $v_{max}$: 2922, 2852, 2100, 1606, 1518, 1279, 1279, 1207, 987, 887 cm$^{-1}$

EXAMPLE 13

Preparation of trans, trans-4-(4-((S)-2-methylbutyl)phenyl) cyclohexyl)-1-n-pentyl-1-silacyclohexane The general procedure of Example 6 was repeated using 4-(4-phenyl-4-(pentyl)-4-silacyclohexyl)cyclohexanone and p-[(S)-2-methylbutyl]phenylmagnesium bromide, thereby obtaining trans, trans-4-(4-((S)-2-methylbutyl)cyclohexyl)-1-n-pentyl)-1-silacyclohexane.

EXAMPLE 14

Preparation of trans, trans-4-(4-(4-trifluoromethoxyphenyl) cyclohexyl)-1-n-propyl-1-silacyclohexane The general procedure of Example 6 was repeated using 4-(4-phenyl-4-(propyl)-4-silacyclohexyl)cyclohexanone and trifluoromethoxyphenylmagnesium bromide, thereby obtaining trans, trans-4-(4-(4-trifluoromethoxyphenyl) cyclohexyl)-1-n-propyl-1-silacyclohexane. The results of NMR and IR analyses are shown below.

$^{13}$C-NMR (CDCl$_3$) δ: 10.16 (s), 14.76 (s), 17.79 (s), 17.97 (s), 28.65 (s), 29.91 (s), 34.70 (s), 43.60 (s), 44.10 (s), 45.91 (s), 120.57 (q), 120.76 (s), 127.96 (s), 146.45 (s), 147.28 (s) ppm IR (KBr disc) $v_{max}$: 2924, 2854, 2108, 1510, 1263, 1225, 1190, 1161, 985, 887 cm$^{-1}$

EXAMPLE 15

Preparation of trans, trans-4-(4-(4-trifluoromethoxyphenyl) cyclohexyl)-1-n-pentyl-1-silacyclohexane The general procedure of Example 6 was repeated using 4-(4-phenyl-4-n-pentyl-4-silacyclohexyl)cyclohexanone and trifluoromethoxyphenylmagnesium bromide, thereby obtaining trans, trans-4-(4-(4-trifluoromethoxyphenyl) cyclohexyl)-1-n-pentyl-1-silacyclohexane. The results of NMR and IR analyses are shown below.

$^{13}$C-NMR (CDCl$_3$) δ: 10.11 (s), 12.17 (s), 13.99 (s), 22.37 (s), 24.12 (s), 28.62 (s), 29.90 (s), 34.68 (s), 35.40 (s), 43.57 (s), 44.08 (s), 45.88 (s), 120.55 (q), 120.76 (s), 127.96 (s), 146.46 (s), 147.26 (s) ppm IR (KBr disc) $v_{max}$: 2924, 2854, 2102, 1510, 1267, 1223, 1194, 1159, 987, 887 cm$^{-1}$

EXAMPLE 16

Preparation of trans, trans-4-(4-(4- chlorophenyl) cyclohexyl)-1-n-propyl-1-silacyclohexane The general procedure of Example 6 was repeated using 4-(4-phenyl-4-n-propyl-4-silacyclohexyl)cyclohexanone and chlorophenylmagnesium bromide, thereby obtaining trans, trans-4-(4-(4-chlorophenyl)cyclohexyl)-1-n-propyl-1-silacyclohexane.

EXAMPLE 17

Preparation of trans, trans-4-(4-n-propyl-4-silacyclohexyl) cyclohexyl-4'-fluorobiphenyl In the same manner as in Example 6, 25 g of 4-(4-fluorophenyl)phenylmagnesium bromide was reacted with 31.5 g of 4-(4-phenyl-4-n-propyl-4-silacyclohexyl) cyclohexanone and the resultant alcohol was dehydrated, followed by catalytic reduction to obtain 4-(4-phenyl-4-n-propyl-4-silacyclohexyl)cyclohexyl-4'-fluorobiphenyl. The biphenyl product was then reacted with iodine monochloride, followed by reduction with lithium aluminohydride to obtain 14.4 g (yield: 36%) of the intended product. The product was subjected to NMR and IR analyses with the results shown below.

$^{13}$C-NMR (CDCl$_3$) δ: 10.13 (s), 14.78 (s), 17.81 (s), 17.95 (s), 28.62 (s), 29.98 (s), 34.66 (s), 43.61 (s), 44.32 (s), 45.91 (s), 115.49 (d), 126.86 (s), 127.28 (s), 128.46 (d), 137.29 (s), 137.75 (s), 146.99 (s), 162.27 (d) ppm IR (KBr disc) $v_{max}$: 2920, 2098, 1493, 1436, 984, 847, 845, 818 cm$^{-1}$

EXAMPLE 18

Preparation of trans, trans-4-(4-n-pentyl-4-silacyclohexyl) cyclohexyl-4'-fluorobiphenyl The general procedure of Example 17 was repeated using 4-(4-phenyl-4-n-pentyl-4-silacyclohexyl)cyclohexanone, thereby obtaining 4-(4-phenyl-4-n-pentyl-4-silacyclohexyl) cyclohexyl-4'-fluorobiphenyl.

$^{13}$C-NMR (CDCl$_3$) δ: 10.11 (s), 12.18 (s), 14.01 (s), 22.36 (s), 24.12 (s), 28.62 (s), 29.98 (s), 34.66 (s), 35.40 (s), 43.62 (s), 44.32 (s), 45.91 (s), 115.49 (d), 126.85 (s), 127.27 (s), 128.45 (d), 137.29 (s), 137.73 (s), 146.98 (s), 162.27 (d) ppm IR (KBr disc) $v_{max}$: 2918, 2098, 1493, 1448, 1236, 985, 847, 818 cm$^{-1}$

EXAMPLE 19

Preparation of trans, trans-4-(4-n-propyl-4-silacyclohexyl) cyclohexyl-3',4'-difluorobiphenyl 12 ml of a tetrahydrofuran solution of 1.0 mole of 3,4-difluorophenylmagnesium bromide was dropped in a mixture of 4.11 g of trans, trans-4-(4-(4-chlorophenyl) cyclohexyl)-1-n-propyl-1-silacyclohexane, 200 mg of 1,3-bis(diphenylphosphino)propane nickel (II) chloride and 50 ml of ethyl ether. The mixture was agitated at room temperature for 18 hours, followed by pouring into a saturated ammonium chloride aqueous solution and extraction with ethyl acetate. The resultant extract was washed with brine, dried and concentrated by a usual manner, followed by purification through silica gel chromatography to obtain 3.52 g (yield: 85%) of the intended product. The product was subjected to NMR and IR analyses with the results shown below.

$^{13}$C-NMR (CDCl$_3$) δ: 10.12 (s), 14.77 (s), 17.80 (s), 17.94 (s), 28.61 (s), 29.95 (s), 34.63 (s), 43.60 (s), 44.33 (s), 45.89 (s), 115.75 (d), 117.39 (d),122.75 (dd), 126.81 (s), 127.41 (s), 136.65 (s), 138.30 (dd), 147.64 (S), 149.71 (dd), 150.47 (dd) ppm IR (KBr disc) v$_{max}$: 2916, 2848, 2104, 1533, 1506, 1279, 985, 889, 845, 818 cm$^{-1}$

EXAMPLE 20

Preparation of trans, trans-4-(4-n-pentyl-4-silacyclohexyl) cyclohexyl-3',4'-difluorobiphenyl The general procedure of Example 19 was repeated using trans, trans-4-(4-(4-chlorophenyl)cyclohexyl)-1-n-pentyl-1-silacyclohexane in place of trans, trans-4-(4-(4-chlorophenyl)cyclohexyl)-1-n-propyl-1-silacyclohexane, thereby obtaining the intended product. The results of NMR and IR analyses of the product are shown below.

$^{13}$C-NMR (CDCl$_3$) δ: 10.10 (s), 12.16 (s), 14.00 (s), 22.36 (s), 24.11 (s), 28.61 (s), 29.95 (s), 34.63 (s), 35.39 (s), 43.60 (s), 44.33 (s), 45.89 (s), 115.75 (d), 117.38 (d), 122.72 (dd), 126.80 (s), 127.40 (s), 136.64 (S), 138.29 (dd), 147.63 (s), 148.27 (dd), 151.91 (dd) ppm IR (liquid film) v$_{max}$: 2918, 2106, 1531, 1506, 1311, 985, 887, 837, 810 cm$^{-1}$ As will be apparent from the foregoing examples, the cyclohexanone compounds of the invention are intermediates useful for preparing liquid crystal compounds. In fact, various types of silacyclohexane-based liquid crystal compounds can be derived from the cyclohexanone compounds.

What is claimed is:

1. A cyclohexanone compound of the following general formula (I)

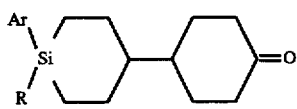

wherein Ar represents a phenyl group or a tolyl group, and R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atom.

2. A process for preparing a cyclohexanone compound of the following general formula (I)

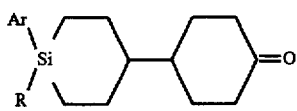

wherein Ar represents a phenyl group or a tolyl group, and R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms, the process comprising the steps of:

subjecting an enamine compound of the following general formula

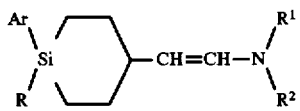

wherein Ar and R have, respectively, the same meanings as defined above, and R$^1$ and R$^2$ represent an alkyl group having from 1 to 4 carbon atoms or R$^1$ and R$^2$ each join to represent a group of —(CH$_2$)$_4$—, —(CH$_2$)$_5$— or —(CH$_2$)$_2$O(CH$_2$)$_2$— thereby completing a cyclic ring along with the nitrogen atom bonded therewith, and methyl vinyl ketone to Michael's addition reaction to obtain Michael's adduct of the following general formula

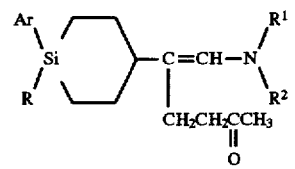

further subjecting the Michael's adduct to intramolecular aldol condensation reaction or hydrolysis to obtain a ketoaldehyde compound of the following general formula

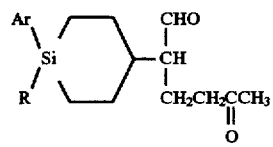

and subjecting the ketoaldehyde compound to intramolecular aldol condensation reaction to obtain a cyclohexenone compound of the following general formula

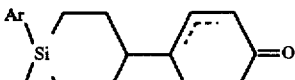

hydrogenating the cyclohexenone compound to obtain a cyclohexanone of the above-indicated general formula (I).

3. A process according to claim 2, wherein the Michael's addition reaction is effected in a solvent under heating to a temperature ranging from 0° to 150° C. in such a way that said methyl vinyl ketone is present at a ratio, to said enamine compound, by equivalent of 1:1 to 5:1.

4. A process according to claim 2, wherein said cyclohexenone is hydrogenated at a temperature of from 0° to 150° C. at a pressure of an atmospheric pressure to 20 kg/cm$^2$ of hydrogen.

5. A process for preparing silacyclohexane-based liquid compound of the following general formula (II)

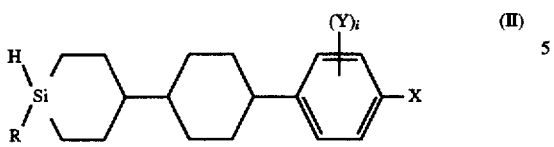

wherein R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms, X represents CN, F, Cl, Br, $CF_3$, $OCF_3$, $OCHF_2$, OCHFCl, $OCF_2Cl$, $CF_2Cl$, $(O)_mCY_1=CX_1X_2$ wherein m is a value of 0 or 1, $Y_1$ and $X_1$ each represent, H, F or Cl, and $X_2$ represents F or Cl, $O(CH_2)_r(CF_2)_sX_3$ wherein r and s are a value of 0,1 or 2 provided that r+s=2, 3 or 4, and X3 represents H, F or Cl, or R or OR wherein R has the same meaning as defined above, Y represents a halogen or $CH_3$, and i is a value of 0, 1 or 2, the process comprising the steps of:

reacting a cyclohexanone of the general formula (I)

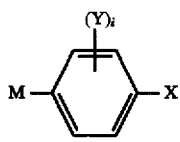

wherein Ar represents a phenyl group or a tolyl group, and R has the same meaning as defined above, with an organometal reagent of the following formula

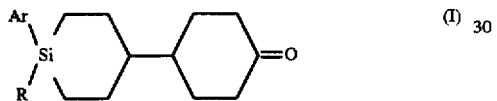

wherein M represents Li MgU, ZnU or $TiU_k(OW)_{3-k}$ wherein U represents a halogen, W represents an alkyl group and k is zero or an integer of 1 to 3, and X, Y and i have the same meanings as defined with respect to the formula (II), thereby obtaining an alcohol compound of the following general formula

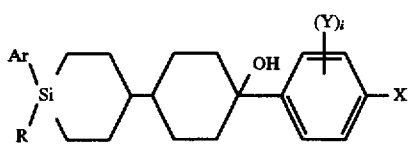

wherein Ar, R, Y, X and i have the same meanings as defined above;

subjecting the compound of the formula in the preceding step to hydrogenolysis, or hydrogenation after dehydration to obtain a compound of the following general formula

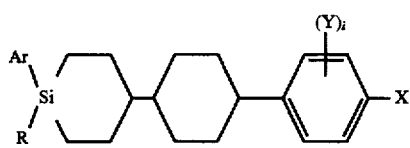

further subjecting the thus obtained compound to de-silylation and reduction to obtain a silacyclohexane-based liquid crystal compound of the afore-indicated general formula (II).

6. A process according to claim 5, wherein the hydrogenolysis is effected at a temperature of from 0° to 150° C. at a pressure of from an atmospheric pressure to 20 kg/cm² of hydrogen in the presence of a catalyst for hydrogenation.

7. A process according to claim 5, wherein said alcohol compound is dehydrated with an acid and then hydrogenated at a temperature of from 0° to 150° C. at a pressure of from an atmospheric pressure to 20 kg/cm² of hydrogen in the presence of a catalyst for hydrogenation.

8. A process according to claim 5, wherein said de-silylation is effected using an electrophilic reagent.

9. A process according to claim 8, wherein the de-silylation is effected after addition of a Lewis acid or under irradiation of light.

10. A process for preparing a silacyclohexane-based liquid crystal compound of the following general formula (III)

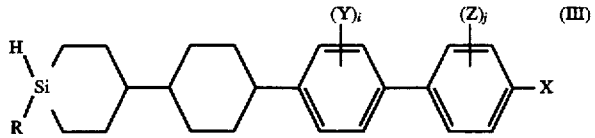

wherein R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms, X represents CN, F, Cl, Br, $CF_3$, $OCF_3$, $OCHF_2$, OCHFCl, $OCF_2Cl$, $CF_2Cl$, $(O)_mCY_1=CX_1X_2$ wherein m is a value of 0 or 1, $Y_1$ and $X_1$ each represent, H, F or Cl, and $X_2$ represents F or Cl, $O(CH_2)_r(CF_2)_sX_3$ wherein r and s are a value of 0, 1 or 2 provided that r+s=2, 3 or 4, and $X_3$ represents H, F or Cl, or R or OR wherein R has the same meaning as defined above, Y represents a halogen or $CH_3$, and i is a value of 0, 1 or 2, Z represents a halogen or $CH_3$, and j represents a value of 0, 1 or 2, the process comprising the steps of: reacting a cyclohexanone compound of the following general formula (I)

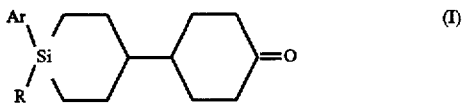

wherein Ar represents a phenyl group or a tolyl group, and R has the same meaning as defined above, with an organometallic reagent of the following general formula

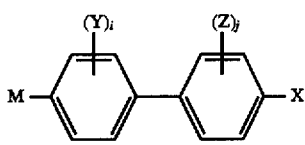

wherein M represents Li MgU, ZnU or TiU$_k$(OW)$_{3-k}$ wherein U represents a halogen, W represents an alkyl group, k is zero or an integer of 1 to 3, X, i and j have the same meanings as defined above, thereby obtaining an alcohol compound of the following general formula

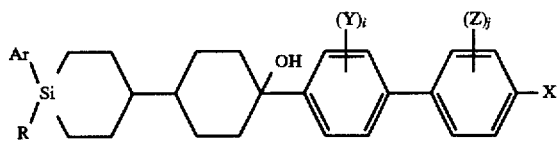

wherein Ar, R, X, Y, Z, i and j have, the same meanings as defined hereinabove;

subjecting the alcohol compound of the above formula to hydrogenolysis, or hydrogenation after dehydration to obtain a compound of the following general formula

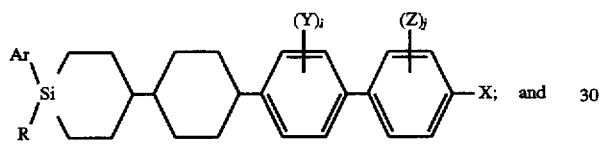

further subjecting the compound of the formula to de-silylation and then reduction to obtain a silacyclohexane-based liquid crystal compound of afore-indicated formula (III).

11. A process according to claim 10, wherein the hydrogenolysis is effected at a temperature of from 0° to 150° C. at a pressure of from an atmospheric pressure to 20 kg/cm² of hydrogen in the presence of a catalyst for hydrogenation.

12. A process according to claim 10, wherein said alcohol compound is dehydrated with an acid and then hydrogenated at a temperature of from 0° to 150° C. at a pressure of from an atmospheric pressure to 20 kg/cm² of hydrogen in the presence of a catalyst for hydrogenation.

13. A process according to claim 10, wherein said de-silylation is effected using an electrophilic reagent.

14. A process according to claim 13, wherein the de-silylation is effectedafter addition of a Lewis acid or under irradiation of light.

15. A process for preparing a silacyclohexane-based liquid crystal compound of the following general formula (III)

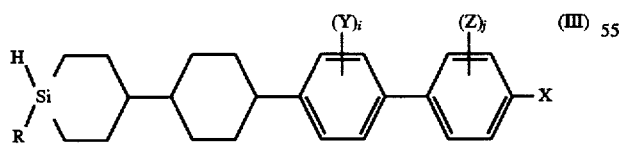

wherein R represents a phenyl group, a tolyl group, a linear alkyl group having from 1 to 10 carbon atoms, a mono or difluoroalkyl group having from 1 to 10 carbon atoms, a branched alkyl group having from 3 to 8 carbon atoms or an alkoxyalkyl group having from 2 to 7 carbon atoms, X represents. CN, F, Cl, Br, CF$_3$, OCF$_3$, OCHF$_2$, OCHFCl, OCF$_2$Cl, CF$_2$Cl, (O)$_m$CY$_1$=CX$_1$X$_2$ wherein m is a value of 0 or 1, Y$_1$ and X$_1$ each represent, H, F or Cl, and X$_2$ represents F or Cl, O(CH$_2$)$_r$(CF$_2$)$_s$X$_3$ wherein r and s are each a value of 0, 1 or 2 provided that r+s=2, 3 or 4, and X$_3$ represents H, F or Cl, or R or OR wherein R has the same meaning as defined above, Y represents a halogen or CH$_3$, and i is a value of 0, 1 or 2, Z represents a halogen or CH$_3$, and j represents a value of 0, 1 or 2, the process comprising the steps of:

reacting a cyclohexanone compound of the following general formula (I)

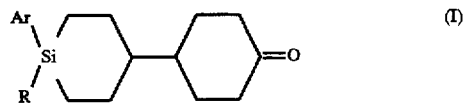

wherein Ar represents a phenyl group or a tolyl group, and R has the same meaning as defined above, with an organometallic reagent of the following general formula

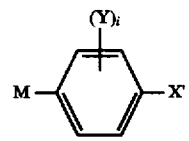

wherein M represents Li MgU, ZnU or TiU$_k$(OW)$_{3-k}$ wherein U represents a halogen, W represents an alkyl group, k is zero or an integer of 1 to 3, and X' represents a halogen, and Y represents a halogen or CH$_3$ and i is a value of 0, 1 or 2 as defined above, thereby obtaining an alcohol compound of the following general formula

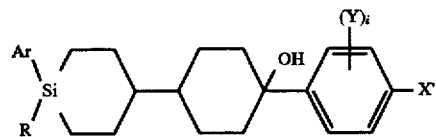

wherein Ar and R have the same meanings as defined hereinbefore;

subjecting the alcohol compound of the above formula to hydrogenolysis, or hydrogenation after dehydration to obtain a compound of the following general formula

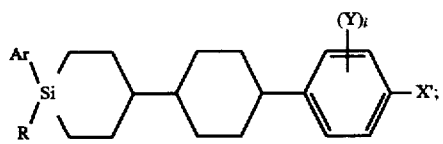

further subjecting the compound of the formula to reaction with an organometal reagent of the following general formula

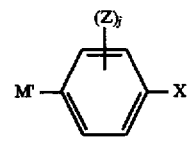

wherein M' represents MgU', ZnU' or TiU'$_k$(OW)$_{3-k}$ in which U' represents a halogen or B(OV)$_2$ in which V represents H or an alkyl group, W and k have the same meanings as defined above, thereby obtaining a compound of the following general formula

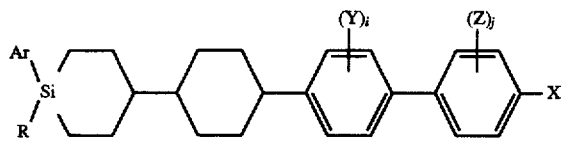

wherein Ar, R, X, Y, Z, i and j have the same meanings as defined hereinbefore; and further subjecting the thus obtained compound to de-silylation and reduction to obtain a silacyclohexane-based liquid crystal compound of the general formula (III).

16. A process according to claim 15, wherein said de-silylation is effected after addition of a Lewis acid or under irradiation of light.

17. A process according to claim 15, wherein M' represents $B(OV)_2$ wherein V is H or an alkyl group, whereupon the reaction with the organometallic compound is effected under basic conditions.

* * * * *